United States Patent [19]

Sato

[11] Patent Number: 4,604,992
[45] Date of Patent: Aug. 12, 1986

[54] ENDOSCOPE SYSTEM

[75] Inventor: Ken Sato, Akigawa, Japan

[73] Assignee: Olympus Optical Company, Ltd., Japan

[21] Appl. No.: 685,322

[22] Filed: Dec. 24, 1984

[30] Foreign Application Priority Data

Dec. 27, 1983 [JP] Japan .................. 58-248948

[51] Int. Cl.⁴ .................................................. A61B 1/04
[52] U.S. Cl. ................................. 128/6; 128/303.1; 128/303.15; 128/395; 358/98
[58] Field of Search ............... 128/4, 6, 303.1, 303.15, 128/395; 358/98; 350/96.26

[56] References Cited

U.S. PATENT DOCUMENTS 4,170,997 10/1979 Pinnow et al. ................. 128/4 X
4,253,447 3/1981 Moore et al. .................... 128/6
4,261,344 4/1981 Moore et al. .................... 128/6
4,408,602 10/1983 Nakajima ..................... 128/303.1

Primary Examiner—William H. Grieb
Attorney, Agent, or Firm—Ostrolenk, Faber, Gerb & Soffen

[57] ABSTRACT

An endoscope system includes a CCD camera of the line transfer type located at and within the distal end of an endoscope. The camera produces and supplies a video output to a television monitor, thus enabling medical treatment with laser radiation while the affected area is under observation. Illumination of the affected area and laser radiation used for the medical treatment, are blocked at selected intervals to prevent them from impinging upon the CCD camera at least during a period of operation when the camera is in a charge transfer mode.

9 Claims, 7 Drawing Figures

ENDOSCOPE SYSTEM

BACKGROUND OF THE INVENTION

The invention relates to an endoscope system, and more particularly, to an endoscope system which includes a solid-state camera mounted within the distal end of an endoscope to produce a video signal which is fed to a television monitor for allowing medical treatment with laser radiation while the monitor is being observed.

An endoscope system including a solid-state camera, comprising by CCD or MOS elements, and mounted within the distal end of an endoscope is described in a number of publications, including U.S. Pat. No. 4,261,344. As can be appreciated the distal end of an endoscope is very space limited which imposes restrictions on the choices of solid-state cameras which can be used. A higher image sensitivity is achieved with larger picture elements upon which light impinges while a higher resolution is achieved by providing more picture elements of wind space. Such requirements must be met with a minimized overall size. In respects of the sensitivity and resolution, these requirements are best met by a solid-state camera which utilizes charge transfer elements such as a CCD. The size of the solid-state camera can be minimized with a line transfer type camera (which will be hereafter referred to as LT type). However, in an LT type solid-state camera an area upon which light impinges is used in common with an area from which a transfer is made. Accordingly, a charge from the light impinging area may be superimposed upon a video signal during a transfer operation, disadvantageously causing a smearing or distortion. To overcome this difficulty, a pulsed light source may be used in an endoscope so that it illuminates the CCD elements during a selected interval while light is intercepted from CCD elements during a transfer operation.

On the other hand, another endoscope arrangement (which may be referred to as a laser-scope) has also been developed which provides not only the ability to observe, but also the capability of medical treatment, by introducing a laser probe into the interior of the endoscope, for example, into the forceps channel thereof, so that laser radiation may be radiated from the distal end thereof toward an object being treated. In such arrangement, it is readily apparent that during the time that medical treatment with laser radiation with the endoscope, the solid-state camera may respond to the radiation if not otherwise blocked so that the smearing phenomenon can be experienced.

As is known, an infrared rejection filter is normally disposed in front of the solid-state camera in order to prevent infrared noise from being input to the camera. However, in medical laser treatment, a YAG laser which produces infrared radiation is used for purposes of treatment, and simultaneously, a He-Ne laser or the like which produces radiation in the visible portion of the spectrum is used to provide guide light for safety purpose since the output radiation from the YAG laser is invisible. Hence, it will be seen that the mere provision of the infrared rejection filter disposed in front of the solid-state camera mounted within the distal end of the endoscope is inadequate for preventing the smearing effect when a CCD camera of LT type is employed.

SUMMARY OF THE INVENTION

It is an object of the invention to provide an endoscope system which prevents smearing from occurring in an LT solid-state camera which utilizes CCD elements.

In accordance with the invention, an arrangement is made such that both the illuminating radiation and the laser radiation are intercepted from incidence upon CCD elements at least during the charge transfer from the latter, thus avoiding the smearing effect and enabling a sharp image to be obtained.

DETAILED DESCRIPTION OF PREFERRED EMBODIMENTS

Figure 1:
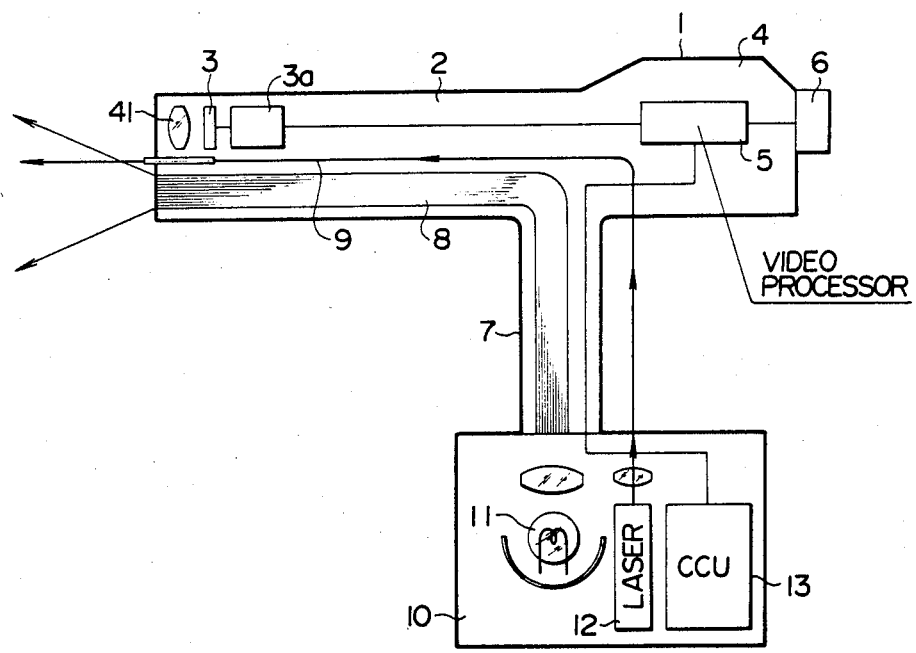
FIG. 1 is a schematic view illustrating generally an endoscope system according to an embodiment of the invention.

Referring to FIG. 1, there is shown the general arrangement of an endoscope system according to the invention. The system includes an endoscope 1 having a portion 2 which is adapted to be inserted into coeloma of a patient. A line transfer type of a solid-state camera 3 which utilizes CCD elements as well as a preamplifier 3a which amplifies an output from the camera 3 are internally housed within the distal end of the endoscope portion 2. The endoscope 1 includes an operating end 4 in which are disposed a video signal processing circuit 5 which processes electrical signal from the camera 3 for forming a television image and an electronic viewfinder 6 which displays the television image through an eyepiece unit.

A universal cord 7 and a light guide 8 extend through the endoscope 1, the guide 8 communicates with the inserted endoscope portion 2. A laser probe 9 which is used for medical treatment with laser radiation is detachably disposed within a channel of the endoscope 1.

The endoscope 1 is connected to a light source unit 10 which includes a lamp 11, a laser oscillator 12 and a central control unit (hereafter referred to as CCU) 13.

Figure 2:
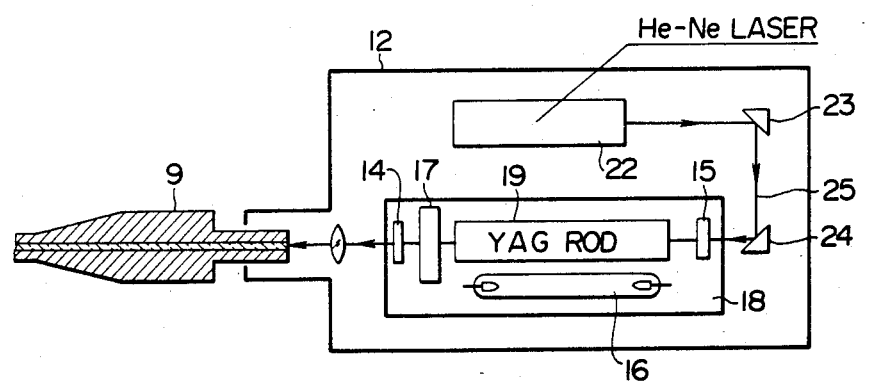
FIG. 2 is a schematic view showing the fundamental construction of laser oscillator used in the endoscope system of FIG. 1.

The construction of the laser oscillator 12 is shown in FIG. 2. Specifically, it includes a YAG laser oscillator 18 comprising a YAG rod 19 having a resonance optical path, and a pair of resonating mirrors 14, 15 disposed in opposing relationship with the opposite end faces of the YAG rod 19 and in alignment with the axis of the optical path. The resonating mirror 14 which is disposed on the output emitting side permits a slight transmission of YAG laser radiation for operating purpose while the resonating mirror 15 disposed on the other side provides a total reflection of YAG laser radiation. An excitation lamp 16 is juxtaposed alongside the YAG rod 19. By illuminating the lamp 16, the YAG rod 19 can be excited. A beam shutter 17 is interposed between the emitting end of the YAG rod 19 and the resonating mirror 14 in alignment with the optical path. It should be noted that the both resonating mirrors 14, 15 are designed to transmit a guide radiation, to be described later.

The laser oscillator 12 also includes a guide radiation generator 22 which produces guide radiation in the form of visible light. The guide radiation generator 22 may comprise He-Ne laser oscillator, for example. The guide radiation is introduced into the YAG laser oscillator 18 in coaxial relationship with the YAG rod 19 thereof through an optical system 25 including a pair of reflecting mirrors 23, 24. Where output radiation from the YAG laser is used for surgical purposes, the radiation has a wavelength of 1060 nm. For purposes of guiding the probe, the output radiation from He-Ne laser which produces guide radiation has a wavelength of 632.8 nm.

Figure 3:
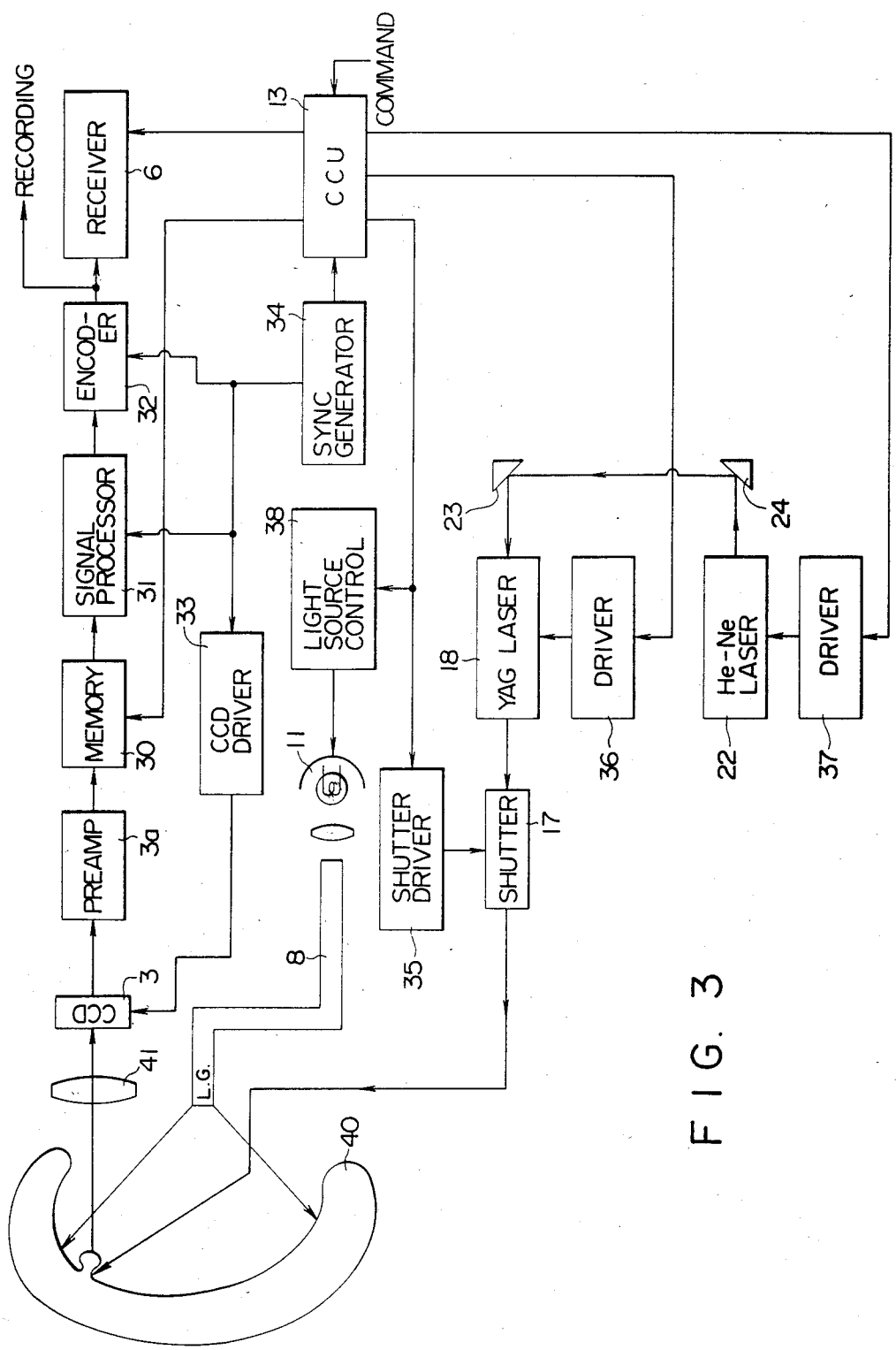
FIG. 3 is a block diagram of an electrical circuit of an endoscope system according to one embodiment of the invention.

Referring to FIG. 3, a circuit arrangement of the endoscope system according to one embodiment will now be described. As shown, the CCD or solid-state camera 3 is connected to the preamplifier 3a, the output of which is fed through a memory 30 to a signal processing circuit 31. The processing circuit 31 is connected to an encoder 32, an output of which is fed to a television receiver 6 and may also be fed to a recorder, not shown, to be stored.

The solid-state camera 3 is driven by a CCD driver 33 which is connected to a sync signal generator 34. An output from the sync signal generator 34 is supplied to the CCU (central control circuit) 13, which produces various outputs supplied to the memory 30, the receiver 6, a shutter drive circuit 35, YAG laser drive circuit 36, He-Ne laser drive circuit 37 and a light source control circuit 38.

Before describing the operation of the circuit arrangement, it is to be noted that the present embodiment utilizes an area sequential color television system. Specifically, the lamp 11 is adapted to produce light of three primary colors R, G and B, which are sequentially switched by the source control circuit 38. Also, the video signal is formulated into a 2:1 interlaced NTSC standard format.

Illuminations R, G and B are sequentially incident upon the light guide 8 from the lamp 11 with a period of 1/180 second. Light emitted from the light guide 8 irradiates an object 40 being examined, an image of which is focussed by an objective lens 41 upon the solid-state camera 3. An output from the camera 3 is amplified by the preamplifier 3a before it is supplied to the memory 30. The memory 30 records the respective video signals corresponding to the colors R, G and B, and delivers the three views simultaneously to the signal processing circuit 31 when three views for these different colors are available. The signal processing circuit 31 performs a variety of corrections and a synthesis of a color signal, a luminance signal and the like, with the processed video signal being supplied to the encoder 32 so as to be encoded into the NTSC signal form. An output from the encoder 32 is input to the receiver 6, which displays the image of an object 40 being examined on the screen of a cathode ray tube or liquid crystal panel or the like.

As mentioned previously, the camera 3 is driven by the CCD driver 33, which is in turn controlled by the sync signal generator 34 to deliver its drive pulse in synchronized relationship. Specifically, the sync signal generator 34 outputs both horizontal and vertical sync signals, and the charge from the source 3 is transferred in accordance with these sync signals. Since the camera 3 reads each view of R, G or B, it follows that the respective views are read out with a period of 1/180 second. The sync signal generator 34 also feeds CCU 13, and accordingly sync signals are delivered to the source control circuit 38 and the shutter drive circuit 35 from CCU 13. These sync signals operate to turn the lamp 11 on and off and to open or close the shutter 17 in synchronized relationship with each other and with a period of 1/180 second. Specifically, the lamp 11 is energized and the shutter 17 is opened during the storage mode of the camera 3, and the lamp 11 is deenergized and the shutter 17 is closed during the transfer mode of the camera 3. This prevents the incidence of any extraneous light or laser radiation upon the light receiving area of the camera 3 during the transfer mode. The sync signal generator 34 also feeds the signal processing circuit 31 and the encoder 32 to achieve a synchronized signal processing operation. The encoder 32 encodes the sync signal into the resulting video signal.

As shown, CCU 13 is connected to the YAG laser drive circuit 36 and to the He-Ne laser drive circuit 37 to control the laser oscillating operation. While not shown, an external keyboard and a foot switch are used to control CCU 13.

An output from CCU 13 is also input to the memory 30 to control it so that views of different colors R, G and B from the camera 3 can be output with a period of 1/60 second to define one field of the image. As mentioned previously, the television image is formatted in a 2:1 interlaced form, and accordingly, the camera 3 and the memory 30 may include a number of elements or locations on the order of 500×500 matrix so as to be compatible with the NTSC television format. However, in the present embodiment, the size of the camera 3 and the memory 30 is minimized even though the resolution is degraded, by reducing the number of horizontal scan lines by one-half or to 250 lines, and a view for one frame is formed by reading out the R, G and B signals from the camera 3 twice.

Alternatively, if the camera 3 has a number of CCD elements which are sufficient to provide 500 horizontal scan lines, the lamp 11 may be energized or deenergized at a period of 1/90 second, and the memory 30, having data corresponding to three views corresponding to the colors R, G and B from the camera 3 stored therein, may provide a line interlaced output.

In this embodiment, the laser radiation is intercepted by the shutter 17 in synchronized relationship with the transfer mode of the camera 3, in a manner similar to the way, the lamp 11 is controlled. This prevents the incidence of extraneous illumination or laser radiation upon the light receiving area of the camera during the transfer mode, enabling the generation of a sharp image which is smearfree.

Figure 4:
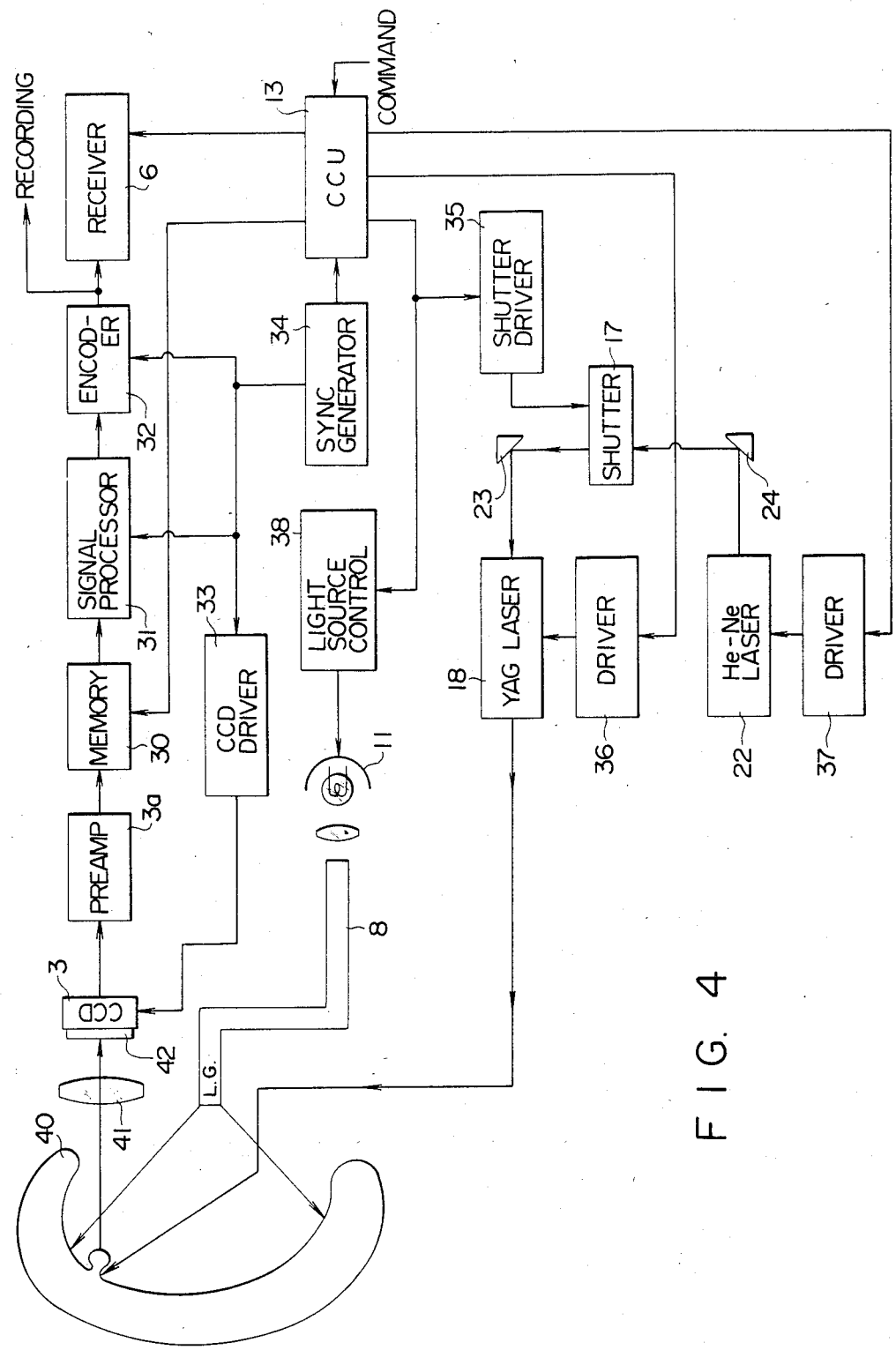
FIG. 4 is a block diagram of an electrical circuit of an endoscope system according to another embodiment of the invention.

An alternative embodiment is shown in FIG. 4 in which an infrared rejection filter 42 is disposed on the input surface of the camera 3 to block the infrared radiation. Corresponding parts illustrated in FIG. 3 will not be redescribed. In the embodiment shown in FIG. 4, the shutter 17 is disposed in the optical path of the laser radiation from He-Ne laser. While this is not illustrated in FIG. 2, it is thus disposed within the optical system 25. The infrared rejection filter 42 intercepts laser radiation from the YAG laser, and hence a continuous irradiation during medical treatment is possible to improving the efficiency of the treatment.

It should be understood that the television format used in the present invention is not limited to the standard NTSC form mentioned above, but that other formats may also be used. The laser radiation which is used for treatment purposes is not limited to infrared radiation. Ultraviolet radiation may also be used. Thus, the radiation wavelengths are not limited to the specific values referred to herein.

Figure 5:
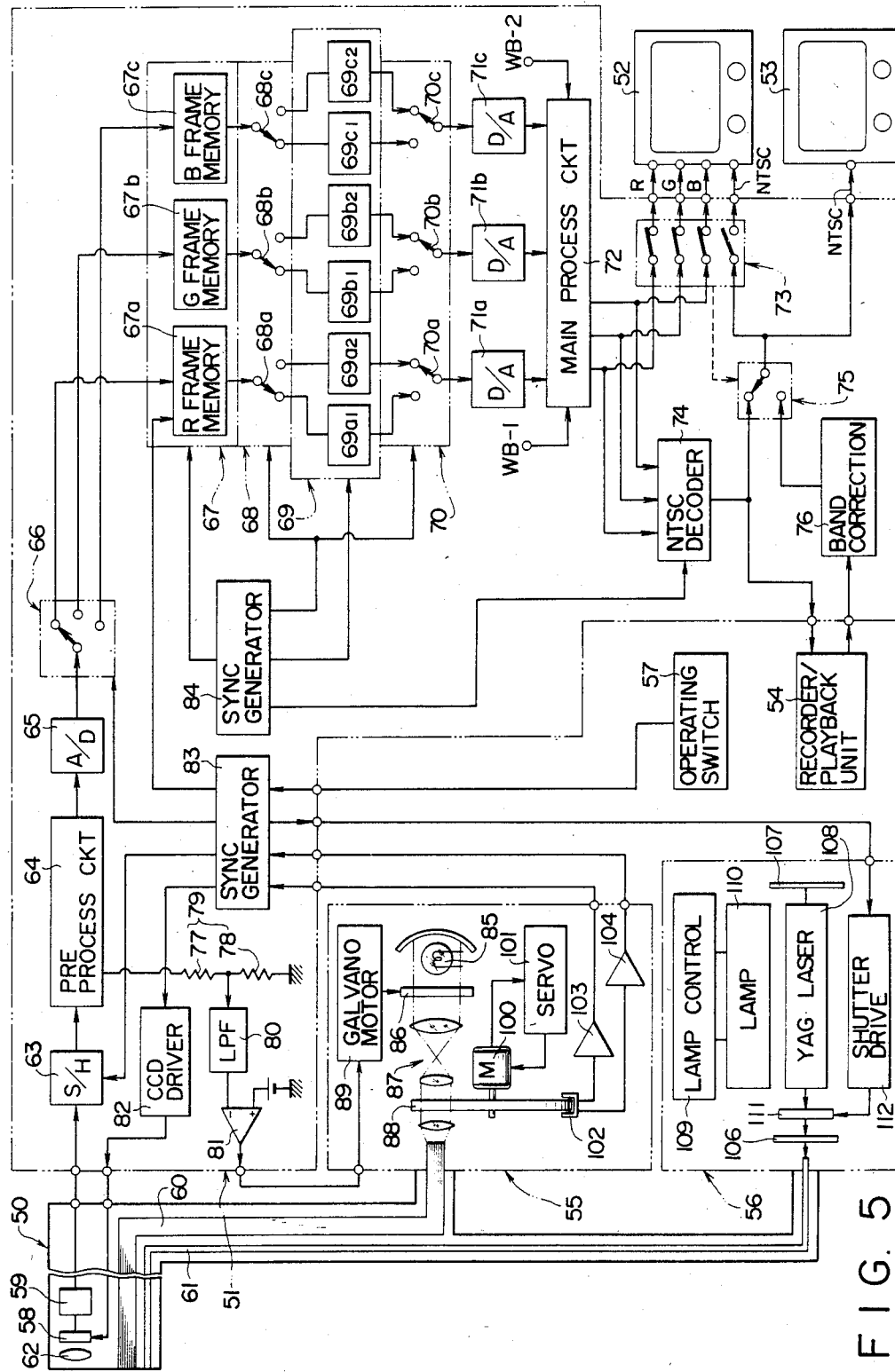
FIG. 5 is a block diagram of an electrical circuit of an endoscope system according to a further embodiment of the invention.

FIG. 5 shows an endoscope system according to a further embodiment of the invention. The endoscope system shown in FIG. 5 comprises an endoscope which is generally indicated by numeral 50, a video processor 51, RGB/NTSC monitor 52, NTSC monitor 53, a recording/playback apparatus 54, a light source unit 55, a laser oscillator unit 56 and an operating switch 57. Disposed within the distal end of the endoscope 50 is a solid-state camera 58 of LT type utilizing CCD elements and which is disposed rearwardly of an objective lens 62 for taking a picture of a coeloma or cavity. An output from the camera 58 is fed through a preamplifier 59 to the video processor 51. A light guide 60 and a laser probe 61 are located internally in the endoscope 50. The laser probe 61 may be located in a forceps channel, for example, for directing laser radiation from the laser unit 56 to the distal end of the endoscope 50 for irradiating an affected part with laser radiation. The light guide 60 comprises a bundle of optical fibers which lead the illuminating light from the light source unit 55 to the distal end for illuminating the interior of the coeloma or cavity.

The video signal supplied to the video processor 51 from the preamplifier 59 is fed through and processed by a sample-and-hold circuit 63, preprocessor 64, an A/D converter 65 and a selector 66 to be supplied to a frame memory 67. The frame memory 67 includes three memory sections 67a, 67b, 67c which are adapted to store views of different colors R, G and B, respectively. The selector 66 also has three output terminals, which are connected to the R, G and B memory sections 67a, 67b and 67c, respectively.

Outputs from the frame memory 67 are supplied to a plurality of 1H memories 69 through a selector 68. It will be seen that a pair of 1H memories 69 are provided for each color component. The selector 68 operates to write data of ones horizontal scanning line into alternate one of the 1H memories, and data is read out from that 1H memory which has stored data therein. Specifically, outputs from the memory sections 67a, 67b and 67c are fed to selector sections 68a, 68b and 68c, respectively. Each of the selector sections 68a, 68b and 68c has a pair of output terminals so that the output from the selector section 68a is selectively supplied to 1H memory sections $69a_1$, $69a_2$, the output from the selector section 68b is selectively supplied to 1H memory sections $69b_1$, $69b_2$, and the output from the selector section 68c is selectively supplied to 1H memory sections $69c_1$, $69c_2$. An output from either 1H memory sections $69a_1$, $69a_2$, as determined by a selector section 70a, is fed to a D/A converter 71a. An output from either 1H memory sections $69b_1$, $69b_2$, as determined by a selector section 70b, is supplied to a D/A converter 71b. An output from either 1H memory sections $69c_1$, $69c_2$, as determined by a selector section 70c, is supplied to a D/A converter 71c. Outputs from the D/A converters 71a, 71b and 71c are fed to a main processing circuit 72 where the white balance is adjusted by multiplying the R and B signals by white balance adjusting signals WB-1 and WB-2, respectively. The R, G and B outputs from the main processing circuit 72 are fed through a switch 73 to R, G and B input terminals of RGB/NTSC monitor 52.

The R, G and B outputs which are demodulated in the main processing circuit 72 are also fed to an NTSC decoder 74, an output of which is fed to a first input terminal of a selector 75 and also to the input terminal of the recording/playback unit 54. A reproduced signal from the recording/playback unit 54 is fed through a band correction circuit 76 to a second input terminal of the selector 75. The selector 75 delivers an NTSC signal, which is then input to NTSC input terminal of RGB/NTSC monitor 52 through the switch 73 and also directly supplied to NTSC input terminal of NTSC monitor 53.

It will be noted that the preprocessing circuit 64 is also connected to a voltage divider 79 formed by resistors 77 and 78, whereby the luminance component of the video signal is fed through a low pass filter 80 and a comparing amplifier 81 to provide automatic illumination control signal which is supplied to the light source unit 55.

The video processor 51 also includes a CCD driver 82 which generates a clock pulse for driving the camera 58. The timing of operation of various circuits within the video processor 51 is controlled by a pair of sync signal generators 83, 84. The sync signal generator 83 receives a signal from the operating switch 57 which controls the irradiation which is supplied from the laser. Outputs from the sync signal generator 83 are fed to the sample-and-hold circuit 63, the selector 66, the frame memory 67, and CCD driver 82. On the other hand, outputs from the sync signal generator 84 are fed to the frame memory 67, the selector 68, the 1H memory 69, the selector 70 and the NTSC decoder 74. It is to be noted that the rate at which data is written into the frame memory 67 is different from the rate at which data is read out from this memory. The write-in operation into the frame memory 67 is controlled by the sync signal generator 83 while the read-out operation from the frame memory 67 is controlled by the sync signal generator 84. It is also to be noted that the selector 68 and the selector 70 are controlled in a manner such that they select different 1H memory sections.

The light source unit 55 includes a lamp 85 which produces illuminating light which is directed into light guide 60. The illuminating light from the lamp 85 is fed through a diaphragm 86, an optical system 87 and a rotary color filter 88 and into the light guide 60. The diaphragm 86 comprises a disc having a given thickness and having a multitude of apertures formed therein which is rotatable by a galvano-motor 89. By changing the angle relative to the optical axis, the size of the aperture controls the amount of light which passes therethrough. The galvano-motor 89 is driven by the automatic illumination control signal from the comparing amplifier 81. As mentioned previously, the automatic illumination control signal depends on the luminance component of the video signal, and the aperture is controlled so that the levels of the luminance signals of different colors are uniform.

Figure 6:
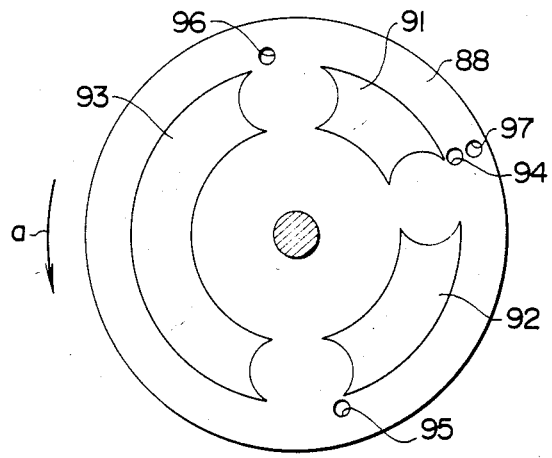
FIG. 6 is a front view of a rotary color filter shown in FIG. 5.

The rotary color filter 88 functions as a shutter and also functions to convert the illuminating light into different colors R, G and B. As shown in FIG. 6, the rotary color filter 88 includes a disc carrying R, G and B color filters 91, 92 and 93 which are spaced apart on a concentric annulus and which have a sequentially increasing angular span. The space between adjacent color filters is used as a shutter for blocking the light incidence upon the camera 58, thereby allowing the signal to be read out from the camera 58. The rotary filter is adapted to rotate in a direction indicated by an arrow a, (counter-clockwise in the example shown), and through-holes 94, 95, 96 are formed in the disc adjacent to the trailing end of the respective color filters 91, 92, 93, are viewed in the direction of rotation, and adjacent to the outer edge of the annulus. The holes 94, 95, 96 serve generating read pulses.

A through-hole 97 is formed in the disc in juxtaposed relationship with and outside the through-hole 94 associated with the R filter 91 for producing a start pulse. The rotary color filter 88 is rotatable by a step motor 100, which is controlled by a produce circuit 101 to rotate at a given speed of rotation. A photodetector 102, comprising light emitting element and light detecting element, is disposed along the edge of the rotary color filter 88 to detect the transmission of light through the through-holes 94, 95, 96 and 97, thus developing the read pulses and the start pulse. The start pulse produced by the photodetector 102 is fed through an amplifier 103 to the sync signal generator 83 within the video processor 51. Similarly, the read pulses are fed through an amplifier 104 to the generator 83.

The laser unit 56 includes a YAG laser 108 which is disposed between a pair of resonating mirrors 106, 107 and which is excitation by an exciter lamp 110 which is in turn controlled by a lamp control circuit 109. The optical path defined between the YAG laser 108 and the resonating mirror 106 may be selectively blocked or opened by a shutter 111 which is connected to a shutter drive circuit 112. In this manner, laser radiation from the YAG laser 108 impinges upon the laser probe 61 in bursts or pulse form. The shutter drive circuit 112 is turned on and off by the sync signal generator 83 located in the video processor 51.

The operation of the foregoing embodiment will now be described with reference to FIGS. 7(A) to (F). The servo circuit 101 causes the step motor 100 to rotate the rotary color filter 88 at a given rate, for example, 30 revolutions per second. During one revolution of the rotary color filter 88, the illuminating light is sequentially colored into R, G and B, as illustrated in FIG. 7(C), and at the termination of the illumination of each color, a read pulse is generated as indicated in FIG. 7(B) and is supplied to the sync signal generator 83. During the time interval which extends from the generation of the read pulse to the initiation of the following illumination with a next color component, the video signal of the respective color component is written into the frame memory 67, as shown in FIG. 7(D). In this manner, an area sequential color television system is achieved. When the illumination of the color R terminates and the read pulse is generated, the start pulse is generated as indicated in FIG. 7(A), and is supplied to the sync signal generator 83.

In response to the start pulse and the read pulse, the sync signal generator 83 controls the laser unit 56 and the camera 58 in the following manner: It is assumed that the lamp control circuit 109 is turned on to excite the YAG laser 108, but that the shutter drive circuit 112 is turned off to cause the shutter 111 to block the optical path to the laser probe 61, thus preventing the incidence of the laser radiation into the laser probe 61. When the operating switch 57 is turned on, the sync signal generator 83 allows the shutter drive circuit 112 to be turned on to thereby move the shutter 111 out of the optical path to the laser probe 61 and thus allow the laser radiation to be incident upon the laser probe 61, in synchronized relationship with the G filter 92 of the rotary color filter 88 converting the illuminating light, as indicated in FIG. 7(E). As a result, the laser radiation irradiates an object being examined in synchronized relationship with the G illumination, to thus treat the object. Accordingly, the object is not irradiated when a readout of signal from the camera 58 occurs, thus effectively preventing the occurrence of a smearing effect. While the YAG laser produces an infrared radiation, if the irradiation takes place during the illumination with the visible light (G), a picture is taken as a visible (green) color, preventing the color balance from being disturbed. Hence, if the He-Ne laser which is used in the previous embodiment to provide guide radiation is not used, the laser radiation from the YAG laser may be in the visible light range, eliminating the need for the provision of two different lasers and, allowing a simplification of the system.

Figure 7:
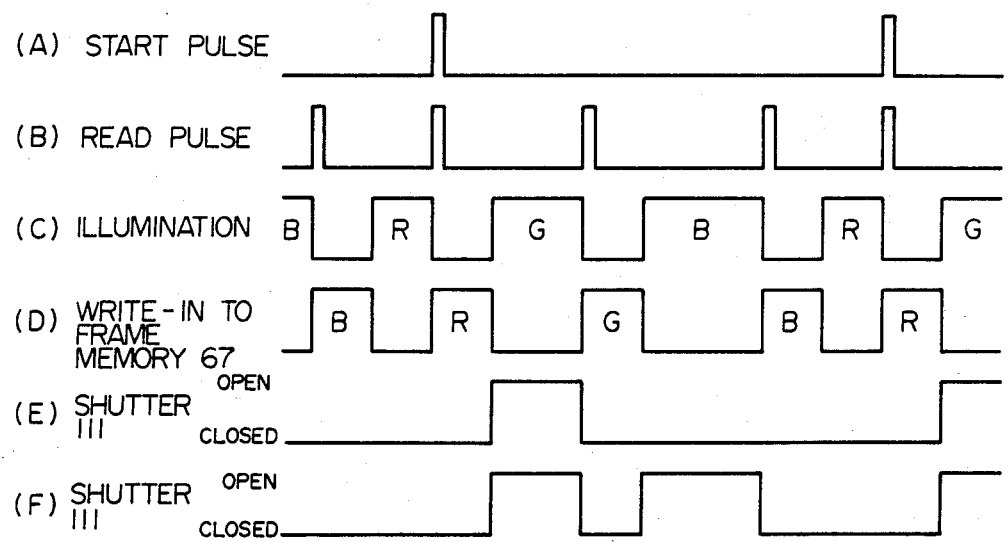
FIGS. 7(A) to (F) are a series of timing charts illustrating various signals appearing at designated points in the electrical circuit of FIG. 5.

It should be understood that the laser irradiation is not limited to the interval during which the illumination of the color G takes place, but that such irradiation may also take place during the illumination of another color, or during the illumination of the colors G and B, as illustrated in FIG. 7(F). In the latter instance, the laser radiation causes a picture to be taken with a cyan color. By increasing the length of the interval allowed for the irradiation, an increase in the intensity of laser radiation is permitted, improving the treatment capability. As mentioned previously, the color filters have different sizes. Accordingly, the intensity of the laser radiation increases in the sequence of R, G, B, R+G, G+B, R+G+B which are used to provide the illumination, if the radiation takes place in synchronized relationship with such illumination. During the illumination of R+G, R+B, G+B and R+G+B, the laser radiation permits a picture to be taken in a yellow, magenta, cyan and white color, respectively.

As discussed above, with this embodiment, an object being treated can be irradiated with output radiation from YAG laser in synchronized relationship with the illumination of R, G and B color in the area sequential scheme, effectively eliminating the occurrence of a smearing effect and retaining an advantage that the YAG laser may be utilized without the concurrent use of He-Ne laser.

What is claimed is:

1. An endoscope system including a line transfer type CCD solid-state camera located within the distal end of an endoscope, said camera providing a video output to a television monitor so that an affected area can be treated with laser radiation while being observed, said system comprising:
   a light source for providing illumination;
   a laser oscillator for producing said laser radiation;
   blocking means for blocking said illumination from said light source and said laser radiation from said laser oscillator from impinging upon said CCD camera at least during a period of operation when said CCD camera is in a transfer mode; and
   locating means for locating and displaying at least a portion of a path followed by said laser radiation on said television monitor.

2. An endoscope system according to claim 1 in which said locating means comprises means for generating visible light and projecting said light coaxially with said path of said laser radiation.

3. An endoscope system according to claim 2 in which said means for generating visual light comprises a He-Ne laser oscillator.

4. An endoscope system according to claim 1 in which said blocking means comprises illumination control means responsive to an output from a sync signal generator for turning said light source off in synchronism with a period when said CCD camera is in a charge transfer mode, and laser radiation control means and a shutter therefore which are responsive to an output from said sync signal generator, and are disposed in the path of said laser radiation and driven by said laser radiation control means, for blocking said path in synchronism with said period.

5. An endoscope system according to claim 1 in which said blocking means comprises illumination control means responsive to an output from a sync signal generator for intercepting said illumination in synchronism with a period when said CCD camera is in charge transfer mode, visible light control means responsive to an output from said sync signal generator and including a shutter driven by said visible light control means, for blocking visible light produced by said locating means in synchronism with said period, and an infrared rejection filter disposed on an input surface of said CCD camera.

6. An endoscope system according to claim 1 in which said locating means comprises a rotatable color filter disposed forwardly of said light source and a motor for rotating said color filter to produce colored illumination in synchronism with the operation of said blocking means and during a time period when said blocking means does not block said laser radiation.

7. An endoscope system according to claim 6 in which said rotatable color filter includes a plurality of differently colored filtered sections including the three primary colors R, G and B, and wherein said laser radiation is projected in synchronism with the use of at least one of said filter sections.

8. An endoscope system according to claim 1 in which said blocking means comprises illumination control means including a rotatable color filter disposed forwardly of said light source and a motor for rotating said color filter, said filter including a shield portion which blocks the path of said illumination in synchronism with a period when said CCD camera is in a charge transfer mode, and laser radiation control means responsive to an output from a sync signal generator and to an output from said illumination control means, for blocking said laser radiation in synchronism with the period during which said shield portion of said rotatable color filter blocks the path of said illumination.

9. An endoscope system according to claim 8 in which said sync signal generator is responsive to an output pulse generated by said illumination control means to provide a sync signal for controlling a charge storage period and a charge transfer period associated with said CCD camera.

* * * * *